(12) United States Patent
Wu et al.

(10) Patent No.: US 7,238,665 B2
(45) Date of Patent: Jul. 3, 2007

(54) PEPTIDE MARKER TARGETING TO NASOPHARYNGEAL CARCINOMA CELL AND APPLICATION THEREOF

(75) Inventors: Han-Chung Wu, Taipei (TW); Chin-Tarng Lin, Taipei (TW); Tong-Young Lee, Taipei (TW)

(73) Assignee: National Taiwan University (TW)

(*) Notice: Subject to any disclaimer, the term of this patent is extended or adjusted under 35 U.S.C. 154(b) by 290 days.

(21) Appl. No.: 10/796,892

(22) Filed: Mar. 9, 2004

(65) Prior Publication Data

US 2005/0010036 A1    Jan. 13, 2005

(30) Foreign Application Priority Data

Jul. 1, 2003    (TW) ............... 92117944 A (51) Int. Cl.
*A61K 38/04*    (2006.01)
(52) U.S. Cl. .......... 514/12; 530/324; 530/327; 530/328
(58) Field of Classification Search ........... 514/12; 530/324, 327, 328
See application file for complete search history.

(56) References Cited

U.S. PATENT DOCUMENTS 6,372,720 B1 *   4/2002   Longmuir et al. ............ 514/44

2002/0172711 A1 *   11/2002   Martin et al. ............... 424/450

FOREIGN PATENT DOCUMENTS

WO    WO 200100225 A1 *   1/2001
WO    WO 200181581 A2 *   11/2001

OTHER PUBLICATIONS

Burgess et al. (J. Cell Biol. 111:2129-2138, 1990).*
Wen et al. (Proc. Natl. Acad. Sci. U.S.A. 98: 4622-4627, 2001).*
Lazar et al. (Mol. Cell Biol. 8:1247-1252, 1998).*
Kunisawa et al. (J. Controlled Release 2005; 105: 344-353).*
Vaage et al. (Cancer; 1994; 73; 1478-1484).*

* cited by examiner

*Primary Examiner*—Shanon Foley
*Assistant Examiner*—Bradon Fetterolf
(74) *Attorney, Agent, or Firm*—Ostrolenk, Faber, Gerb & Soffen, LLP (57) ABSTRACT

The present invention provides a peptide marker targeting to nasopharyngeal carcinoma (NPC) cells and application thereof. The peptide binds specifically to the cell surface of NPC cells. After conjugated with liposome containing chemotherapeutic drugs, such peptides deliver chemotherapeutic drugs to the tumor cells specifically and destruct tumor cells without damaging normal tissues and organs. Furthermore, such peptide is applied as a detector in the development of NPC diagnosis kit.

12 Claims, 6 Drawing Sheets
(1 of 6 Drawing Sheet(s) Filed in Color)

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial
<220> FEATURE:
<223> OTHER INFORMATION: The Peptide Marker Targeting to Nasopharyngeal
      Carcinoma Cell

<400> SEQUENCE: 1

Arg Leu Leu Asp Thr Asn Arg Pro Leu Leu Pro Tyr
1               5                   10

<210> SEQ ID NO 2
<211> LENGTH: 3
<212> TYPE: PRT
<213> ORGANISM: Artificial
<220> FEATURE:
```

```
-continued

<223> OTHER INFORMATION: The Peptide Marker Targeting to Nasopharyngeal
      Carcinoma Cell

<400> SEQUENCE: 2

Leu Pro Tyr
1
```

PEPTIDE MARKER TARGETING TO NASOPHARYNGEAL CARCINOMA CELL AND APPLICATION THEREOF

BACKGROUND OF THE INVENTION

1. Field of the Invention

The present invention relates to a tumor peptide marker and application thereof, particularly a tumor peptide for applying in targeted delivery of chemotherapeutic drugs specifically to nasopharyngeal carcinoma (NPC) cells.

2. The Prior Arts

Nasopharyngeal carcinoma (NPC) occurs in high incidence among Chinese living in South China, Taiwan and Singapore. Genetic and environmental factors are important in the development of NPC. The etiological factors have not been clearly identified yet, but factors such as the habits of eating salted fish, Chinese herbs and long term exposure to the sulphuric acid vapor have been related to NPC induction. In addition, Epstein-Barr (EB) virus has also been found to be closely associated with NPC.

The medical treatments for NPC, such as radiotherapy, surgical removal and chemotherapy have been applied for more than 30 years. The 5 year survival rate has been improved to be more than 90% in the localized NPC cases in some medical centers. However, the survival rate drops to below 50% in advanced stage NPC patients. Efforts such as high dose chemotherapy plus bone marrow stem cell injection and targeting therapy are employed to improve the effectiveness of chemotherapy.

Most cancer cells and their normal host cells usually share many common features which makes the former cells lack of molecular targets. Many of chemotherapy's most severe toxic effects stem directly from their non-selective nature; most available compounds that inhibit tumor cell growth also inhibit the growth of normal cells. Therefore, chemotherapeutics with high toxicity including doxorubicin could not be regularly applied in cancer therapy because of owing selectivity for cancer cells which resulted increased toxicities against normal tissues such as bone marrow, gastrointestinal tract and hair follicles. Side effects that occur as a result of toxicities to normal tissues mean that anticancer chemotherapeutic drugs are often given at sub-optimal doses, resulting in the eventual failure of therapy; often accompanied by the development of drug resistance and metastatic disease. Therefore, ligand-targeted therapy with drugs that target the molecular differences between tumor and normal cells promise to be less toxic and more effective than our current drugs. Such advances are leading to new applications in cancer therapy.

Conventional chemotherapy is limited by the toxicity toward normal cells. It will be greatly improved if drugs were delivered to cancer cells directly and kept away from sensitive normal cells. Generally small-molecule compounds contain large volumes of distribution which spread into the whole body and are easily accumulated in normal tissues (Speth et al., 1988). This may result in the eventual failure of chemotherapy accompanied with the development of drug resistance or metastatic disease.

Through encapsulation of drugs in a macromolecular carrier, such as a liposome, the volume of distribution is significantly reduced and the local concentration of drug in the tumor area is increased (Drummond et al., 1999), resulting in decreases of dosage and nonspecific toxicities and increase the effectiveness of drug dosage.

Liposomes are aqueous compartments enclosed by a lipid bilayer which protect the drugs from being metabolized and inactivated in plasma. Due to the size limitations in the transportation of large molecules or carriers across healthy endothelium, the drugs encapsulated in liposomes are accumulated to a reduced extent in healthy tissues (Mayer et al., 1989; Working et al., 1994). Liposomes contain a lipid membrane that is relatively impermeable to both amphipathic and highly water-soluble molecules at physiological temperatures (37° C.). This feature is important in drug stability either during storage or in plasma. The internal aqueous space of liposomes can also be used to entrap a variety of chemotherapeutic drugs like doxorubicin or diagnostic dyes (Drummond et al., 1999).

Many small molecules can be delivered to the target sites with targeted immunoliposomes recently (Ahmad et al., 1993; Martin et al., 1982; Papahadjopoulos et al., 1991). The formulations of liposomes in early stage were removed rapidly from blood circulation by the reticuloendothelial system, thus preventing the liposomes from reaching the target sites. Liposomes containing various lipid derivatives of polyethylene glycol (PEG) have resulted in improved circulation time and tumor localization (Papahadjopoulos et al., 1991).

Though the abovementioned approaches in cancer targeting therapy decrease the toxicity toward normal tissues more or less in chemotherapy, the clinical effects are still not ideal. Currently, an important advance in cancer targeting therapy is to identify peptide markers and tumor-associated ligands that afford tumor detection and drug limited toxicity.

SUMMARY OF THE INVENTION

A primary object of the present invention is to provide a peptide marker targeting to nasopharyngeal carcinoma cell and application thereof. Such peptide recognizes and binds to the surface ligands of NPC cells specifically. In combination with liposome and chemotherapeutic drugs improves the efficacy of chemotherapy and reduces the drug dosage.

Another object of the present invention is to provide a peptide marker applied as a detector in the development of nasopharyngeal carcinoma cell (NPC) diagnosis kit.

In order to achieve the foregoing objects, phage display technology is employed to identify the phages that could specifically interact with the cell surface of NPC cell line. After several rounds of biopanning, phages showed highly specific binding activity toward NPC cell line were isolated. These candidate phage clones were sequenced and aligned by GCG software. One of the clones which could bind specifically to NPC cells was termed L-peptide (SEQ ID NO: 1).

To further confirm the specific binding of L-peptide, synthetic L-peptide was used to compete with L-phage for the same binding sites of NPC cells. Results showed that L-peptide could inhibit the binding of L-phage on the NPC cell surface. In addition, it is the L-phage displayed peptide but not the phage itself or any other parts of the phage that binds to the NPC cell surface.

Although the L-phage could specifically bind to the NPC cells, the application in diagnosis and other fields is limited. Therefore the inventors synthesize peptides with the same sequences to mimic the phage-binding activity. The binding activity was confirmed in vitro with biotin-labeled L-peptide using immunohistochemistry. It is shown that L-peptide could bind to NPC cell lines and biotin-labeled L-peptide could bind to NPC cells in a dose-dependent manner in the ELISA assay, whereas the control peptide did not react with NPC cells. These results suggest that the phage-displayed L-peptide could be applied as a good target deliverer for NPC chemotherapy.

On the other hand, all the chemotherapeutic drugs are highly toxic to normal tissues and cells in human body if injected directly. Liposomal drug-delivery system is used to avoid the injury to the normal tissue and cells. When antitumor drugs are packaged in liposomes, the toxicity is reduced. The ability of translocation across the cell membrane is another critical point for drug delivery. Therefore, peptides that could be internalized by cells are also important in the present invention.

L-peptide was attached to liposome through conventional methods to confirm the binding ability of L-peptide-liposome complex (abbrv. L-peptide-Lipo) to target protein of NPC cells. The results showed that L-peptide-Lipo is able to bind specifically to the NPC cell surface and can be taken into the tumor cell by endocytosis.

The L-peptide-Lipo could encapsulate chemotherapeutic drugs, such as doxorubicin in the present invention. The compound L-peptide-conjugated Liposome-doxorubicin is abbreviated as L-peptide-Lipo-Dox thereafter. The binding and cytotoxicity of L-peptide-Lipo-Dox to NPC cells were studied in comparison with Liposome-doxorubicin (abbrv. Lipo-Dox). It is shown that L-peptide-Lipo-Dox was more effective than Lipo-Dox in killing NPC cells. This indicates that the L-peptide in L-peptide-Lipo-Dox carries the Lipo-Dox to NPC cells specifically, whereas Lipo-Dox without L-peptide could not bind specifically to the tumor cell.

To test the binding ability of L-peptide-Lipo-Dox in vivo, NPC cells were injected into SCID mice to establish the NPC mice model. Whether L-peptide binds specifically to tumor cells in vivo was determined with this mice model. Xenograft tumor tissue was shown to contain a higher titer of L-phage than other organs such as heart, lung, and brain. This indicates that L-phage has higher affinity to tumor tissue but not to other normal organs. Furthermore, L-phage was only localized in tumor mass, not in brain, lung, and heart from immunohistochemical experiments. It is therefore concluded that L-phage can bind to xenograft tumor cells specifically but not to the normal tissue and cells.

When L-peptide-Lipo-Dox was applied in the therapeutic experiments, L-peptide-Lipo-Dox clearly enhanced therapeutic efficacy in NPC xenograft animal models. There were significant differences in tumor sizes and tumor weights between L-peptide-Lipo-Dox and Lipo-Dox treatments in tumor growth, especially in the experiment group with multiple doses after 48 days (P<0.001). During the whole experiments, the mice treated with L-peptide-Lipo-Dox showed less side effects than those with Lipo-Dox, and all mice treated with L-peptide-Lipo-Dox had normal body weights and unchanged organs.

In summary, we identified a novel L-peptide which is capable to bind to NPC cell surface specifically both in vitro and in vivo through screening on a phage-displayed random peptide library in the present invention. This peptide could be conjugated to the liposomes containing doxorubicin and leads the Lipo-Dox specifically to the NPC tumor cell surface. This liposome delivery system allows for the killing of NPC tumor cells in vivo. L-peptide therefore is a very good target deliverer for drug delivery to NPC cells. The drug dosage used is reduced to one fifth in the system.

For more detailed information regarding advantages and features of the present invention, examples of preferred embodiments will be described below with reference to the drawings. Both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The related drawings in connection with the detailed description of the present invention to be made later are described briefly as follows, in which.

DETAILED DESCRIPTION OF THE PREFERRED EMBODIMENT

Figure 1:
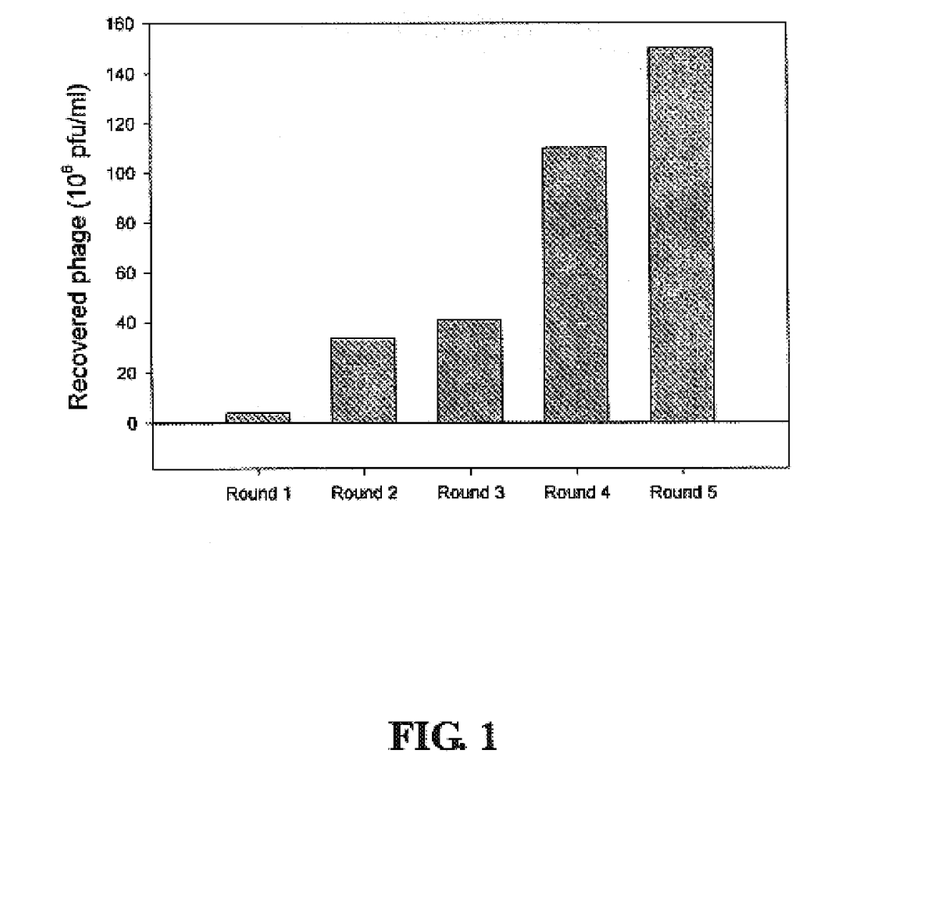
FIG. 1 is a bar graph display of data showing the number of specific phages isolated after biopanning of a phage displayed peptide library for 5 rounds with NPC-TW04 NPC cells. Phages isolated showed specific binding activity toward NPC cell line.

The screening procedures in the present invention are based on a phage displayed peptide library of 12 residues purchased from New England BioLabs (New England BioLabs, Inc. Beverly, Mass., USA). This library expresses the randomized sequence as a fusion of the pIII coat protein, resulting in display of the peptide on the exterior surface of the phage virion. As shown in FIG. 1, at the fifth round of biopanning, the recovery rate of the phages increase 40-fold over that of the first round.

Several NPC-reacted phage clones were selected by ELISA assay. NPC-reacted phage clones were further characterized by DNA sequencing. The inserted DNA fragment was consisted of 36 nucleotides and accordingly encoded 12 amino acids. Through alignment of phage-displayed peptide sequences using GCG software, as shown in Table 1, nine of them had the consistent residue Pro, five of nine phage clones showed the consensus amino acid residues, Leu and Pro. Two of nine phage clones showed a consensus motif of Leu-Pro-Tyr (SEQ ID NO: 2).

Figure 2:
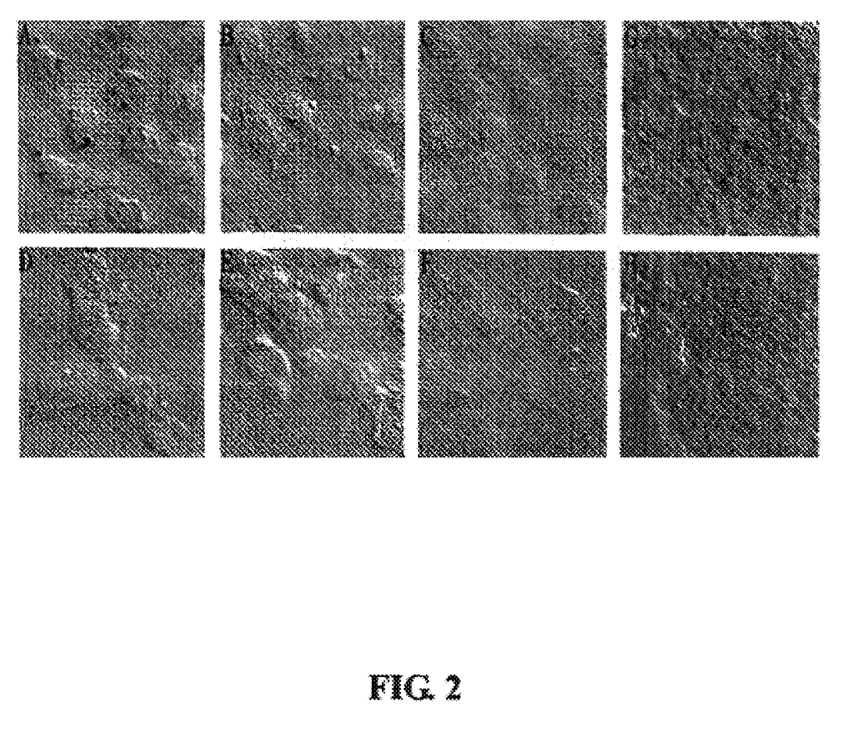
FIG. 2 is a graph showing immunolocalization of candidate phage on cancer cell lines and NPC biopsy specimens.
A: NPC-TW01 NPC cells treated with L-phage;
B: NPC-BM-1 NPC cells treated with L-phage;
C: NPC-TW01 NPC cells treated with phage of control group;
D: Ca9-22 oral cancer cells treated with L-phage;
E: CaSki cervical cancer cells treated with L-phage;
F: normal nasal mucosa cells treated with L-phage;
G: L-phage bound to NPC tissue specimens; and
H: Phage from control group bound to NPC tissue specimens.

The binding ability of these nine candidate phage clones to the cells of NPC cell lines, other cancer cell lines, human nasal mucosal cells or fibroblast was compared using immunohistochemistry. As shown in Table 2, the cellular binding specificities of the nine phage clones varied widely. The phage clone 1-29, which was termed L-phage thereafter, showed the best binding specificity among all the candidates to the tested NPC tumor cell lines, including NPC-TW 01 cell (FIG. 2A), NPC-CGBM-1 cell (FIG. 2B) and other NPC lines such as NPC-TW 03 and 04.

To further confirm that this binding was specific not only to NPC culture cell lines but also to NPC biopsy tumor cells, L-phage was incubated with paraffin sections of NPC tumors. FIG. 2 is a graph showing immunolocalization of candidate phage on cancer cell lines and NPC biopsy specimens. It is shown that L-phage bound to the NPC biopsy section (FIG. 2G, arrowhead) and did not bind to other cancer cell lines such as oral cancer (SAS) cell line (FIG. 2D), uterine cervical cancer (CaSki) cell line (FIG. 2E), and normal nasal mucosal cells (FIG. 2F). On the other hand, the control phage could neither bind to NPC-TW 01 line (FIG. 2C) nor to NPC biopsy specimen (FIG. 2H).

Figure 3:
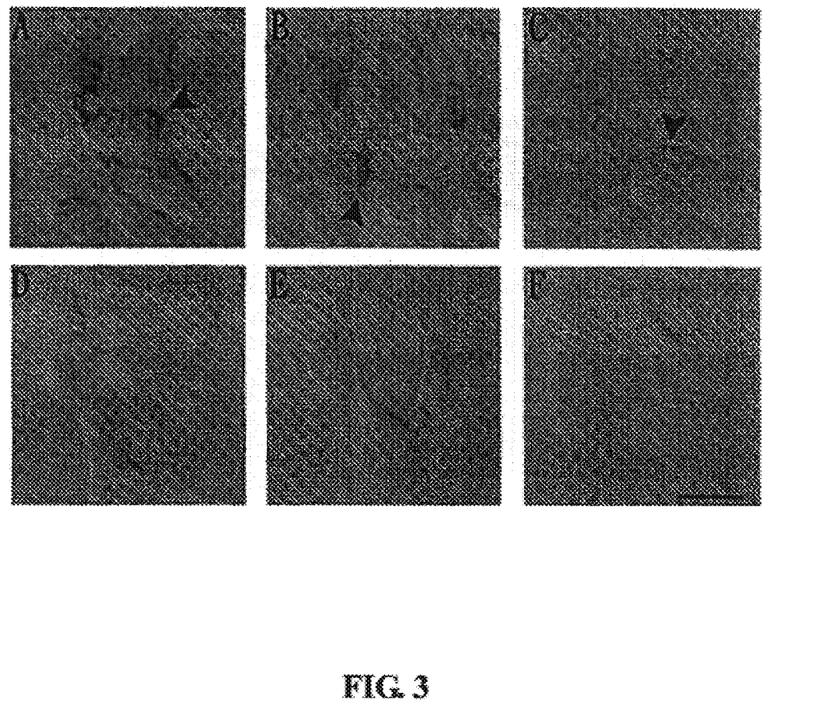
FIG. 3 is a graph showing immunolocalization of L-peptide on different cancer cell lines.
A: NPC-TW04 NPC cells;
B: NPC-TW07 NPC cells;
C: NPC-CGBM-1 NPC cells;
D: Oral carcinoma cells (SAS; an oral squamous carcinoma cells)
E: Normal nasal mucosa cells (NNM); and
F: Fibroblast cells.

In addition, to determine if the binding was mediated through the displayed peptide sequence SEQ ID NO:1, the peptide displayed by L-phage was chemically synthesized and labeled with biotin. The specific binding ability of the biotin-labeled L-peptide with either cancer or normal cells was evaluated. It is shown that NPC cell lines including NPC-TW 04, 07, and NPC-CGBM-1 exhibited reaction products (FIGS. 3A, 3B, 3C: arrows), which represents the binding between L-peptide and cell surface, whereas the oral cancer cell line SAS (FIG. 3D), normal epithelial cells (FIG. 3E) and fibroblasts (FIG. 3F) could not react with the biotin-labeled L-peptide. The biotin-labeled control peptide showed no binding activity either.

Figure 4:
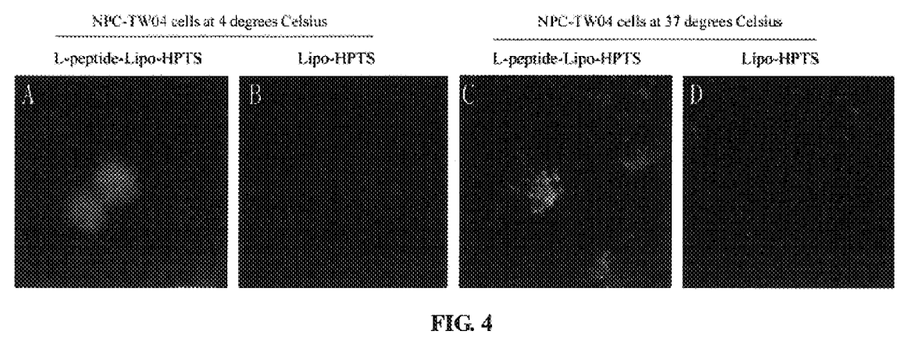
FIG. 4 is a graph showing immunofluorescence staining of L-peptide-liposome-HPTS complex on NPC cells.
A: L-peptide-liposome-HPTS complex was incubated at 4° C. for 90 minutes (mins).
B: Control group (liposome-HPTS complex) was incubated at 4° C. for 90 mins;
C: L-peptide-liposome-HPTS complex was incubated at 37° C. for 90 mins;
D: Control group (liposome-HPTS complex) was incubated at 37° C. for 90 mins.

To explore the ability of L-peptide binding to its target protein on the plasma membrane could be endocytosed by NPC cells, the binding and uptake of L-peptide-liposomes to NPC cells were studied by immunofluorescence microscopy. NPC-TW 04 cells were incubated with fluorescent dye HPTS filled liposome, either HPTS-encapsulated L-peptide liposomes (L-peptide-Lipo-HPTS) or liposomes (Lipo-HPTS) at 4° C. or 37° C. for 90 mins. As shown in FIG. 4, the fluorescence was observed on the cell surface when cells were treated with L-peptide-Lipo-HPTS at 4° C. for 90 mins (FIG. 4A). The punctuated fluorescence was brighter, distributed broadly in the cytoplasm surrounding the nuclei when the cells were treated with L-peptide-Lipo-HPTS at 37° C. for 90 mins (FIG. 4C). But there was no any fluorescence observed in control Lipo-HPTS (FIG. 4B). While Lipo-HPTS groups bound the cytoplasm nonspecifically when treated at 37° C. (FIG. 4D). These data strongly

TABLE 1

Alignment of phage-displayed peptide sequences selected by NPC-TW04 cells.

| Phage clone | Phage-displayed peptide sequence[a] | |
|---|---|---|
| 1-19 | FPSKTGAFVPFS | (SEQ ID NO: 3) |
| 1-35 | NNSQKPAPVSPF | (SEQ ID NO: 4) |
| 1-31 | TKNMLSLPVGPG | (SEQ ID NO: 5) |
| 1-8 | RHLPTLFAPTPT | (SEQ ID NO: 6) |
| 1-37 | QLSPVLARHNIS | (SEQ ID NO: 7) |
| 1-39 | PRGVWUMSLPH | (SEQ ID NO: 8) |
| 1-18 | LPLTSLMPLGLH | (SEQ ID NO: 9) |
| 1-44 | SVSLPYANLATH | (SEQ ID NO: 10) |
| 1-29 (L-phage) | RLLDTNRPLLPY | (SEQ ID NO: 1) |

[a]Phage-displayed consensus amino acids are shown in boldface.

TABLE 2

Binding of nine candidate phage clones to different cell types[a]

| | 1-8 | 1-11 | 1-18 | 1-19 | 1-29 (L-phage) | 1-37 | 1-39 | 1-41 | 1-44 | Control Phage |
|---|---|---|---|---|---|---|---|---|---|---|
| NPC-TW 01 | +/− | + | ++ | ++ | +++ | +++ | ++ | ++ | ++ | +/− |
| NPC-TW 03 | ND | ND | − | ND | ++ | ND | ++ | ND | +/− | − |
| NPC-TW 04 | ++/+ | ++/+ | +/− | +++ | ++ | ++ | ++ | ND | +++ | +/− |
| NPC-CG-BM-1 | − | ND | +/− | ++ | ++/+ | ++ | +++ | ND | + | − |
| Oral Cal-27 | − | ND | − | − | − | − | − | ND | − | − |
| Oral Ca9-22 | + | + | +/− | − | +/− | +/− | ++ | ND | ND | − |
| CaSki | − | − | − | − | − | − | − | − | + | − |
| Hep 2B | ND | − | − | ND | − | +/− | ++ | ++/+ | ++ | − |
| NNM-11 | − | − | +/− | − | +/− | − | − | ND | + | − |
| NNM-13 | − | +/− | − | − | +/− | − | +/− | ++/+ | + | − |
| Fibroblast | ND | − | − | − | − | ND | ND | ND | − | − |

[a]ND: No Detection;
(+++), a value of reaction 40~60%;
(++), a value of reaction 30~40%;
(++/+), a value of reaction 20~30%;
(+), a value of reaction 10~20%;
(+/−), a value of reaction 5~10%;
(−), a value of reaction below 5%.

support that L-peptide-Lipo-HPTS liposomes enter the cytoplasm through endocytosis and stay in the cytoplasm.

Figure 5:
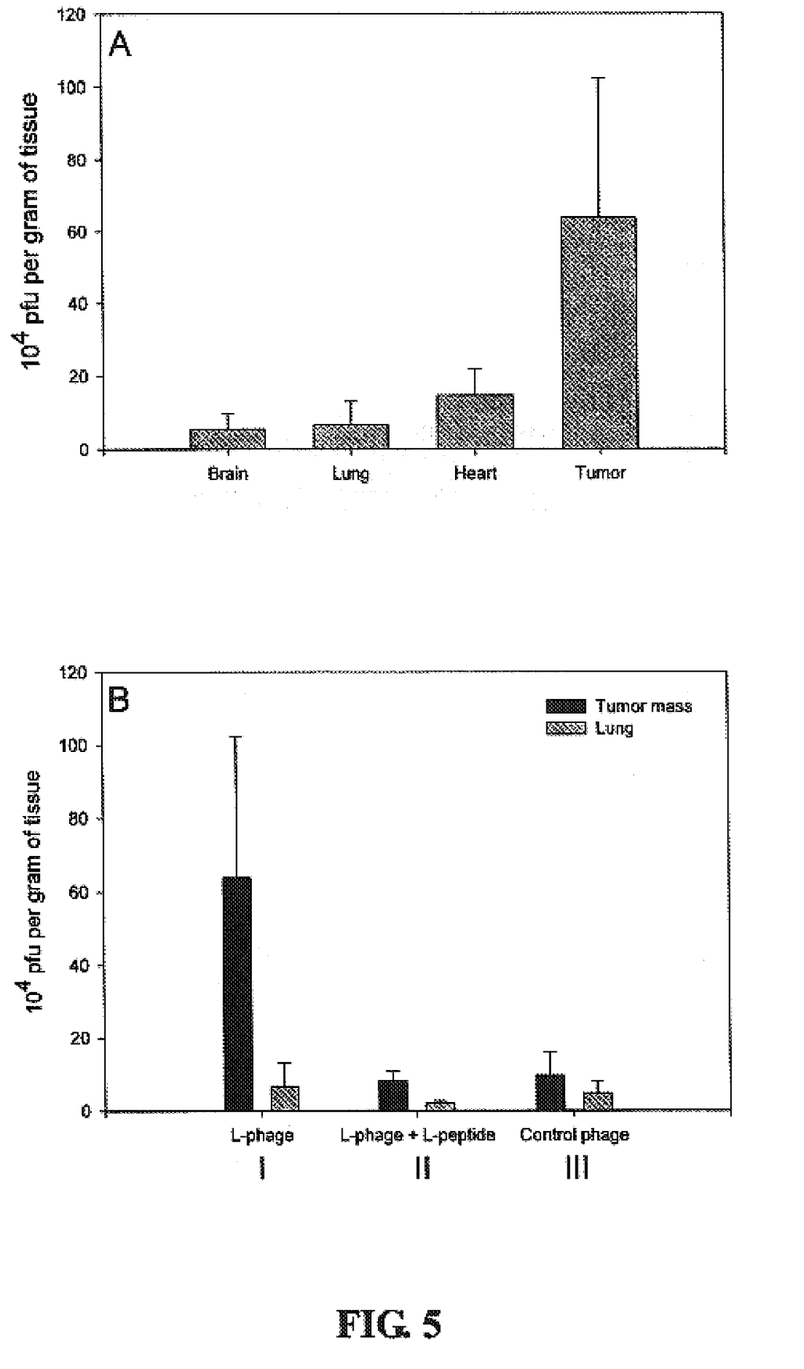
FIG. 5 is a bar graph display of data showing the recovery of tumor-targeting L-phage from SCID mice bearing NPC xenograft tumor and normal tissue.

To verify the targeting of L-phage in vivo, $10^9$ pfu L-phage were injected into the mice bearing with size-matched NPC-TW 01-derived tumor through the tail vein. Concentrations of L-phages were determined in tumor and other organs thereafter. As data shown in FIG. 5, L-phages were specifically targeted in tumor mass since the concentration was 10-fold higher than in other organs, including brain, lung, and heart (FIG. 5A), whereas the control phages and unrelated phage (R3-17) revealed no specific targeting ability in tumor mass. Furthermore, it was shown that co-injection of synthetic free L-peptide with L-phage decreased the recovery of L-phage from tumor mass. Accordingly, tumor targeting of L-phage is specifically inhibited by L-peptide (FIG. 5B).

To determine whether the NPC tumor targeting peptide (L-peptide) improves the therapeutic index of cancer chemotherapeutics, L-peptide combined with doxorubicin is injected into SCID mice.

After 10 days, the mice bearing size-matched NPC-TW 01-derived tumor (~50 mm$^3$) were randomly assigned to different treatment group (4-9 mice per group). Treatments with L-peptide-Lipo-Dox and Lipo-Dox or PBS were administered i. v. at one doxorubicin dose of 5 mg/kg (4-5 mice/group).

Tumor size was significantly decreased in L-peptide-Lipo-Dox treated group in comparison with Lipo-Dox group and PBS groups ($p<0.05$). Furthermore, tumor mass was also significantly decreased in L-peptide-Lipo Dox treated group.

Figure 6:
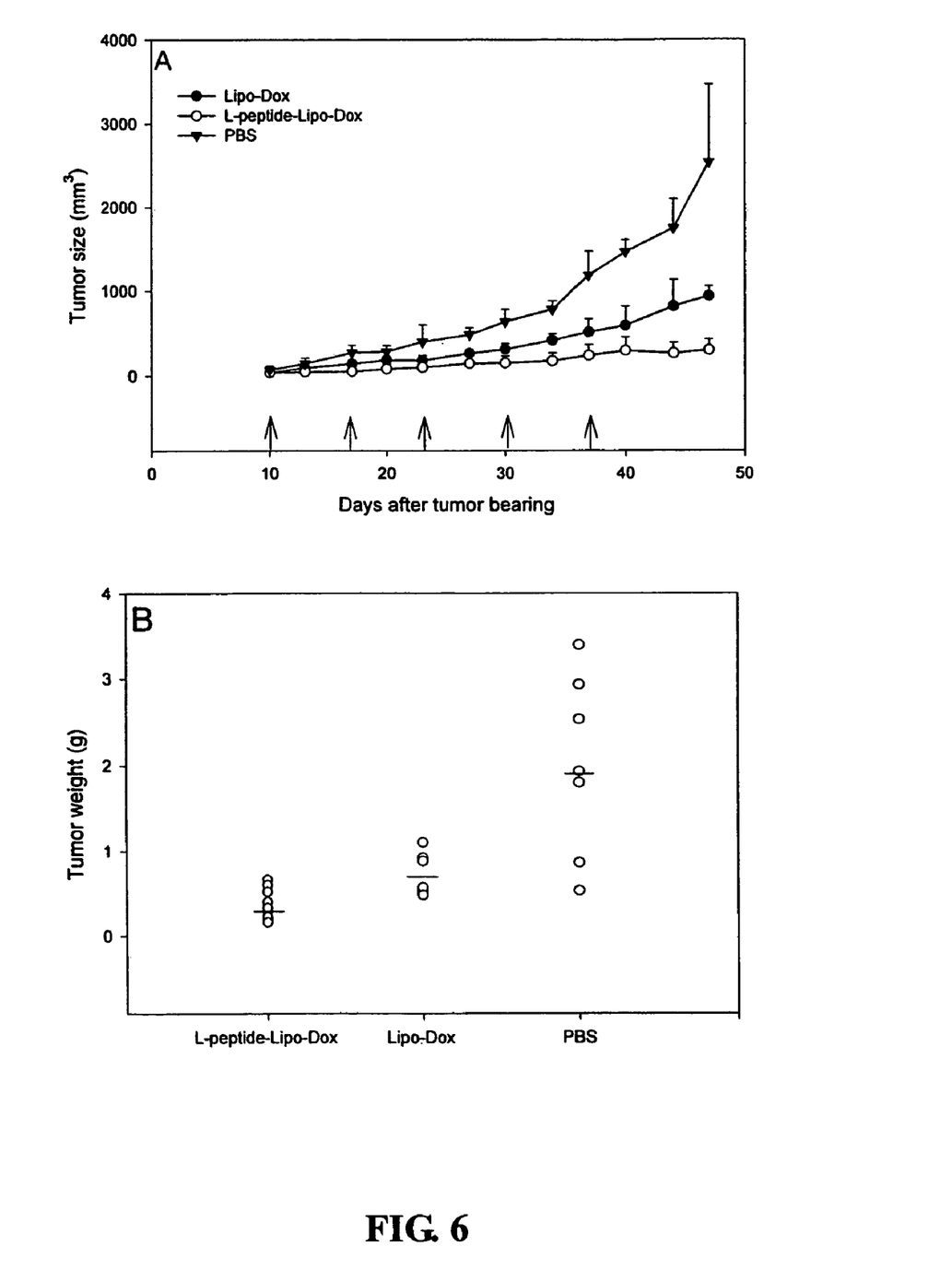
FIG. 6 is a graph showing the tumor size and tumor mass of SCID mice bearing NPC xenografts treated with L-peptide-Lipo-DOX, Lipo-DOX and PBS. Panel A shows the tumor size and panel B shows tumor mass after treatment, respectively.

FIG. 6 is a graph showing the tumor size and tumor mass of SCID mice bearing NPC xenografts treated with L-peptide-Lipo-DOX, Lipo-DOX and PBS. After multiple-dose administration (doxorubicin was given for 5 times, and the total dosage of doxorubicin is 5 mg/kg.) Tumor sizes were significantly smaller in L-peptide-Lipo-Dox treated groups than in Lipo-Dox groups and PBS groups ($p<0.001$) (FIGS. 6A, 6B). Furthermore, tumor volume and tumor weight in L-peptide-Lipo-Dox treated group were also smaller (FIGS. 6A, 6B). That means L-peptide-Lipo-Dox inhibits tumor growth more effectively than Lipo-Dox does.

EXAMPLE 1

Biopanning of a Phage Displayed Peptide Library

The present invention is based on ex vivo screening of phage displayed peptide libraries purchased from New England BioLabs (New England BioLabs, Inc. Beverly, Mass., USA) for specific ligands. $5\times10^6$ of NPC cells (NPC-TW 04) and normal nasal mucosa cells (NNM-13) were placed on 10-cm Petri dish respectively. The culture medium was replaced with 5 ml of DMEM (Dulbecco's modified Eagle medium) containing 1% BSA before biopanning, and the Petri dishes were placed at 4° C. for 30 mins. Then $5\times10^{12}$ plaque-forming units (pfu) of UV-treated inactive control phage (helper phage) were added to confluent cultures of NPC-TW 04 and NNM-13 cells separately at 4° C., followed by addition of $5\times10^{10}$ pfu of M13 phage peptide library PhD-12 (New England BioLabs). The library was biopanned on NPC-TW 04 cells after subtracted with NNM-13 cells 3 times, each time lasted for 1 h at 4° C. Internalized phages were recovered by 2 ml of lysis buffer after washed with cold PBS for three times to remove unbound phages. The recovered phages were amplified in *Escherichia coli* ER2537 culture (New England BioLabs, Mass.). These phages were subjected to five rounds of biopanning with NPC-TW 04 cells. As shown in FIG. 1, the final phage clones increased the binding activity to NPC-TW 04 cells.

EXAMPLE 2

Identification of NPC Specific Phage Clones by ELISA and DNA Sequence Analysis

NPC-TW 04 cells were plated on 96-well enzyme-linked immunosorbent assay (ELISA) plates and cultivated overnight. The cells were washed twice with serum-free DMEM, and then incubated with blocking buffer (serum-free DMEM containing 1% BSA) at 37° C. for 30 mins.

Phages ($10^9$ pfu) selected from Example 1 were added to the above mentioned plates and incubated at 4° C. for 2 hrs, followed by cold PBS washes. Then the plates were incubated with 1:1000 diluted horseradish peroxidase (HRP)-conjugated anti-bacteriophage M13 antibody solution in blocking buffer at 4° C. for 1 hrs. The plates were rinsed with PBS buffer thee times and incubated with the peroxidase substrate o-phenylenediamine dihydrochloride (OPD; Sigma, Germany). The reaction was stopped with 3N HCl, and the plates were read using a microplate ELISA reader at 490 nm. Phage clones with higher binding activity to NPC cells were screened.

The amplified phage clones selected were precipitated with 1/6 volume of polyethylene glycol-NaCl solution [20% (w/v) PEG-8000 and 2.5M NaCl]. The precipitated phage pellets were resuspended in 100 µL of iodine buffer (10 mM Tris-HCl, pH 8.0; 1 mM EDTA; 4M NaI) at room temperature for 10 mins after adding 250 µL of ethanol. Phage DNA was isolated from the pellet after centrifugation at 12,000×g for 10 mins, washed with 70% ethanol, dried, and resuspended in 50 µl distilled water. The DNA sequences of purified phages were determined according to the dideoxynucleotide chain termination method with an automated DNA sequencer (ABI PRISM 377, Conn.). The phage-displayed peptide sequences were translated and aligned using GCG program.

The DNA fragments inserted comprise 36 nucleotide bases that can be translated into 12 amino acids. Through alignment of phage-displayed peptide sequences using GCG software, as shown in Table 1, nine of them had the consistent residue Pro, five of nine phage clones showed the consensus amino acid residues, Leu and Pro. Two of nine phage clones showed a consensus motif of Leu-Pro-Tyr (SEQ ID NO: 2).

EXAMPLE 3

Binding Assay of Specific Phage Clones

All cancer cell lines, normal nasal epithelia cells and fibroblasts were plated on cover glasses and cultured to about 80% confluence. These cover slips were washed with serum-free DMEM twice and incubated in the blocking buffer containing $10^{11}$ pfu of UV-treated inactive control phage at 37° C. for 30 mins. Then they were washed with PBS twice, treated with 1% hydrogen peroxide at 4° C. for 10 mins and rinsed with cold PBS.

$10^9$~$10^{10}$ pfu of purified phage (including L-phage) were added to each cover glasses containing blocking buffer and then incubated at 4° C. for 1 hrs. After washed with cold PBS buffer for thee times, HPR-labeled mouse anti-M13 monoclonal antibody diluted 1:50 in blocking buffer was added for 1 hrs at 4° C.

The cover slips were washed with cold PBS buffer for thee times, fixed with 3% formaldehyde (prepared with phosphate buffer), rinsed with cold PBS twice, then immersed in 0.05% 3,3'-diaminobenzidine-4 HCl in 0.2 M Tris-HCl buffer, pH 7.4 (DAB solution) for 5 mins and transferred to DAB solution containing 0.01% hydrogen peroxide for 40 seconds, washed with PBS and mounted with 50% glycerol in PBS.

The specific binding abilities of these nine candidate phage clones varied widely, as shown in Table 2. FIG. 2 is a graph showing immunolocalization of candidate phage on cancer cell lines and NPC biopsy specimens. The phage clone No. 1-29, which was termed L-phage thereafter, showed the best binding specificity among all the candidates to the NPC tumor cell lines tested including NPC-TW 01 cell lines (see FIG. 2A), NPC-CGBM-1 cell line (see FIG. 2B) and other NPC cell lines, such as NPC-TW 03 and 04. Other phage clones expressed less binding specificity in comparison to L-phage.

EXAMPLE 4

Specific Binding of Biotin-labeled L-peptide to NPC Cell Lines

NPC cells were cultured on cover slips, washed with serum-free DMEM twice and incubated in blocking buffer at 37° C. for 30 mins. After incubation, the cover glasses were washed with cold PBS twice, treated with 1% hydrogen peroxide at 4° C. for 10 mins, and rinsed with cold PBS.

Biotin-labeled L-peptide (abbrev. Biotin-L peptide) and biotin-labeled control peptides (abbrve. Biotin-control-peptide) with concentration of 10 μg/ml were added to these cover glasses and kept at 4° C. for 1 hr and then rinsed with cold PBS twice.

Then the cover slips were further incubated with 1:50 dilution of goat anti-biotin antibody (Vector, Calif.) in the blocking buffer for 1 hr at 4° C. and washed twice with cold PBS.

Biotinylated horse anti-goat antibody (ABC kit, Vector) diluted 1:100 in blocking buffer was added and incubated at 4° C. for 1 hrs and then the slips were rinsed with cold PBS twice.

Then these cover slips were reacted with avidin-biotin-peroxidase complex agent (Vector, Calif.) for 30 mins, fixed in 3% paraformaldehyde in PBS for 10 mins, washed and immersed in DAB solution for 5 mins, then transferred to DAB solution containing 0.01% hydrogen peroxide for 40 seconds, and placed in PBS containing 50% glycerol after washed with PBS.

The results were shown in FIG. 3. Specific reaction products were observed in NPC cell lines, including NPC-TW 04, 07 and NPC-CGBM-1 (arrows in FIGS. 3A, 3B, 3C), whereas no reaction product observed in oral carcinoma cell line (SAS) (FIG. 3D), normal nasal epithelia cells (FIG. 3E) and fibroblast cells (FIG. 3F). That is, NPC cell lines reacts with biotin-labeled L-peptide, but not oral carcinoma cell line (SAS), normal nasal epithelia cells and fibroblast cells.

EXAMPLE 5

Binding Specificity of L-peptide Conjugated Liposome Containing HPTS (L-peptide-lipo-HPTS)

Small unilamellar vesicles were prepared using reverse-phase evaporation. EPC, cholesterol and PEG-DSPE (containing 20% NH-PEG3400-DSPE or not) in the molar ratio of 2:1:0.2, were pressed repeatedly though polycarbonate membrane filters in the order of 0.1 μm and 0.05 μm pore size. Vesicles were filled with 30 mM HPTS, and then L-peptide was conjugated to vesicles.

NPC-TW 04 cells were incubated at 4° C. or 37° C. for 90 mins with HPTS-encapsulated L-peptide liposomes (L-Lipo-HPTS) or liposomes (Lipo-HPTS) which were diluted in growth medium containing 53 μg of peptide concentration per 100 ml medium. After treatment, cells were counter stained Hoechst 33258 (Molecular Probe). Unbound liposomes were removed by 3 washes with cold PBS and mounted with mounting solution (Vector, Calif.). Then cover slips were examined under a Leica DM microscope.

As shown in FIG. 4, the fluorescence was observed on the cell surface when cells were treated with L-peptide-Lipo-HPTS at 4° C. for 90 mins (FIG. 4A). The punctuated fluorescence was brighter, distributed broadly in the cytoplasm surrounding the nuclei when the cells were treated with L-peptide-Lipo-HPTS at 37° C. for 90 mins (FIG. 4C). But there was no any fluorescence observed in control Lipo-HPTS (FIG. 4B). While Lipo-HPTS groups bound the cytoplasm nonspecifically when treated at 37° C. (FIG. 4D). These data strongly support that L-peptide-Lipo-HPTS liposomes enter the cytoplasm through endocytosis and stay in the cytoplasm.

EXAMPLE 6

The Recovery of Tumor-targeting L-phage From SCID Mice Bearing NPC Xenograft Tumor and Normal Tissue SCID mice, with age between 8 and 10 weeks and body weights ranging from 18 to 22 grams, were obtained from the Animal Center in National Taiwan University College of Medicine (Taipei, Taiwan). These mice were injected with $1 \times 10^7$ NPC-TW 01 cells. After 1 to 2 week, the mice bearing size-matched NPC-TW 01-derived tumor (0.5~1 cm in diameter) were injected with $10^9$ pfu L-phage or control phage through the tail vein. Eight to ten mins following the injection, the mice were treated with diethyl ether to induce anesthesia. Then the mice were perfused with 50 ml PBS to wash out unbound phages. Organs and tumor were removed from treated mice, weighted respectively and washed with PBS-PI (proteinase inhibiter; Roche, Germany) (10 ml PBS/one tablet). These organ and tumor samples were homogenized and incubated with 0.5 ml overnight culture of RE2738 bacterial for 40 mins at 37° C. to elute the specific reacted phage particles. The phage particles were diluted with LB medium to $10^2$ to $10^6$ pfu after washing, and placed on agar plates containing 1 mg/l of IPTG and X-gal. After 12 to 16 h, the colonies were counted. In peptide inhibition experiment, $10^9$ pfu of L-phage and 100 μg of L-peptide were co-injected to animals, and phage R3-17 (unrelated phages from library, with a display peptide sequence of TLATTASPDSAQ (SEQ ID NO: 11)) was used in control group.

As data shown in FIG. 5, the L-phage showed clear targeting ability in tumor mass, which is 10 folds concentrated than other organs, including brain, lung, and heart (FIG. 5A), whereas the control phages and unrelated phage R3-17 revealed non-targeting ability in tumor mass. Recovery of L-phage from tumor mass decreased when synthetic free L-peptides were simultaneous injected (FIG. 5B). Therefore tumor targeting effect of L-phage was specific due to ligand inhibition.

EXAMPLE 7

SCID mice bearing tumors as described in Example 6 were injected with $1\times10^7$ NPC-TW 01 cells. After 10 days, the mice bearing size-matched NPC-TW 01-derived tumor (~50 mm$^3$) were randomly assigned to two treatment groups. L-peptide-Lipo-Dox or Lipo-Dox was administered through the tail veins at one doxorubicin dose of 5 mg/kg (4-5 mice/group) or at 5 doses of 1 mg/kg. The total dosage of doxorubicin is 5 mg/kg. The same volume of PBS without L-peptide-Lipo-Dox was used in the control groups. The measurement of body weights and tumor sizes of the mice was taken twice per week. Tumor volume was calculated with the following formula:

Tumor volume=tumor length×(tumor width)$^2$×0.52

After 48 days, all animals were sacrificed and tumor masses were removed and weighted. The differences of average tumor volume and tumor weight are analyzed using Student's t-test.

In single-dose administration experiment, tumor sizes were significantly decreased in L-peptide-Lipo-Dox treated group when compared to Lipo-Dox group and PBS groups ($p<0.05$). Furthermore, tumor weights were also significantly decreased in L-peptide-Lipo Dox treated group.

In multiple-dose administration experiments, tumor sizes were significantly smaller in L-peptide-Lipo-Dox treated groups than in Lipo-Dox groups and PBS groups ($p<0.001$) (FIGS. 6A, 6B). Furthermore, there is smaller tumor volume and tumor weight in L-peptide-Lipo-Dox treated group (Table 3). These results demonstrate that L-peptide-Lipo-Dox inhibits tumor growth more effectively than Lipo-Dox does.

Several preferred embodiments of the present invention are described in detail above with reference to the drawings annexed. It should be understood that these examples are intended to be illustrative only and that the present invention is not limited to the conditions or materials recited therein.

TABLE 3

| | Specific binding of biotin-labeled L-peptide to different cell type[a] | | | | | | | | | |
|---|---|---|---|---|---|---|---|---|---|---|
| Cell line | NPC-TW 01 | NPC-TW 02 | NPC-TW 03 | NPC-TW 04 | NPC-TW 05 | NPC-TW 06 | NPC-TW 07 | NPC-TW 08 | NPC-HOME-1 | NPC-CGBM-1 |
| Biotin-labeled L-peptide | + | ++ | − | ++ | ++ | +++ | ++ | +++ | − | +++ |
| Cell line | NPC-CNE-1 | NPC-CNE-2 | CaSki | Hep 2B | SAS | Ca 9-22 | NNM-11 | NNM-13 | NNM-14 | Fibroblast |
| Biotin-labeled L-peptide | +++ | − | + | − | − | − | − | − | − | − |

[a](+++), a value of reaction 35~50%;
(++), a value of reaction 20~35%;
(+), a value of reaction 5~20%;
(−), a value of reaction below 5%.

What is claimed is:

1. An isolated peptide marker binding specifically to nasopharyngeal carcinoma (NPC) cells, wherein the amino acid sequence of the peptide marker comprises an amino acid sequence as set forth in SEQ ID NO:1.

2. A liposome comprising the peptide of claim 1.

3. A chemotherapeutic drug complex comprising the peptide marker of claim 1, wherein the chemotherapeutic drug complex binds to NPC cells specifically.

4. A chemotherapeutic drug complex according to claim 3, wherein the chemotherapeutic drug complex comprises doxorubicin.

5. An isolated peptide marker according to claim 1, wherein the peptide comprises the ability to lead a liposome to NPC cells.

6. An isolated peptide marker according to claim 5, wherein the peptide guides the liposome to the NPC cell and enters nasopharyngeal carcinoma cell through endocytosis.

7. An isolated peptide marker according to claim 1, wherein the peptide marker is applied as a detector in the development of NPC cell diagnosis kit.

8. A complex targeted specifically to NPC cells comprising an isolated peptide marker, wherein the amino acid sequence of the peptide marker comprises an amino acid sequence as set forth in SEQ ID NO:1.

9. A complex according to claim 8, wherein the complex comprises a chemotherapeutic drug.

10. A complex according to claim 9, wherein the chemotherapeutic drug comprises doxorubicin.

11. A complex according to claim 8, wherein the complex comprises a liposome.

12. A complex according to claim 8, wherein the complex enters NPC cells through endocytosis.

* * * * *